(12) United States Patent
Kim et al.

(10) Patent No.: US 9,582,091 B2
(45) Date of Patent: Feb. 28, 2017

(54) METHOD AND APPARATUS FOR PROVIDING USER INTERFACE FOR MEDICAL DIAGNOSTIC APPARATUS

(71) Applicant: SAMSUNG MEDISON CO., LTD., Gangwon-Do (KR)

(72) Inventors: Hyoung-Jin Kim, Seoul (KR); Mi-Jeoung Ahn, Seoul (KR); Jae-Moon Jo, Seongnam-si (KR); Dong-Gyu Hyun, Gwangju-si (KR)

(73) Assignee: SAMSUNG MEDISON CO., LTD., Gangwon-Do (KR)

( * ) Notice: Subject to any disclaimer, the term of this patent is extended or adjusted under 35 U.S.C. 154(b) by 0 days.

(21) Appl. No.: 14/449,602

(22) Filed: Aug. 1, 2014

(65) Prior Publication Data

US 2015/0054761 A1 Feb. 26, 2015

(30) Foreign Application Priority Data

Aug. 23, 2013 (KR) ........................ 10-2013-0100580

(51) Int. Cl.
| | |
|---|---|
| *G09G 5/00* | (2006.01) |
| *G06F 3/041* | (2006.01) |
| *G06F 3/0488* | (2013.01) |
| *G06F 3/01* | (2006.01) |
| *G06F 3/0481* | (2013.01) |
| *G06F 3/0484* | (2013.01) |

(Continued)

(52) U.S. Cl.
CPC .............. *G06F 3/041* (2013.01); *G06F 3/017* (2013.01); *G06F 3/0488* (2013.01); *G06F 3/04815* (2013.01); *G06F 3/04845* (2013.01); *G06F 3/04886* (2013.01); *G06F 19/3406* (2013.01); *G06T 7/0012* (2013.01); *G06T 15/00* (2013.01); *G06F 19/321* (2013.01); *G06F 2203/04101* (2013.01); *G06F 2203/04104* (2013.01); *G06F 2203/04108* (2013.01)

(58) Field of Classification Search
CPC ...... G06F 3/017; G06F 3/041; G06F 3/04815; G06F 3/04845; G06F 3/0488; G06F 3/04886; G06F 19/3406; G06F 2203/04101; G06F 2203/04104; G06F 2203/04108; G06T 15/00; G06T 7/0012
USPC .................... 345/156–178, 592, 676, 684
See application file for complete search history.

(56) References Cited

U.S. PATENT DOCUMENTS

| | | |
|---|---|---|
| 8,237,654 B2 | 8/2012 | Kang |
| 2006/0077179 A1 | 4/2006 | Hsu et al. |

(Continued)

FOREIGN PATENT DOCUMENTS

| | | |
|---|---|---|
| KR | 2008-0106265 A | 12/2008 |

OTHER PUBLICATIONS

Extended European Search Report issued in European Application No. 14162631.7, dated Jan. 23, 2015.

*Primary Examiner* — Nelson Rosario
(74) *Attorney, Agent, or Firm* — McDermott Will & Emery LLP

(57) ABSTRACT

A user interface (UI) providing method and apparatus that increase the usability of a control panel and quickly and conveniently provide a desired UI to a user. The UI providing method includes detecting a gesture of a hand of a user, determining a touch input UI that corresponds to the detected gesture and is displayed on a screen, and adjusting and displaying the touch input UI on a basis of a distance from the screen to the hand.

19 Claims, 10 Drawing Sheets

(51) Int. Cl.
*G06T 7/00* (2006.01)
*G06T 15/00* (2011.01)
*G06F 19/00* (2011.01)

(56) References Cited

U.S. PATENT DOCUMENTS

| | | |
|---|---|---|
| 2009/0021475 A1 | 1/2009 | Steinle et al. |
| 2010/0315413 A1 | 12/2010 | Izadi et al. |
| 2011/0296333 A1 | 12/2011 | Bateman et al. |
| 2012/0119988 A1 | 5/2012 | Izumi |
| 2012/0229377 A1 | 9/2012 | Kim et al. |
| 2013/0106898 A1* | 5/2013 | Saint-Loubert-Bie et al. ............... 345/592 |
| 2013/0321286 A1* | 12/2013 | Petruzzelli et al. .......... 345/173 |
| 2014/0028567 A1* | 1/2014 | Park ....................... G06F 3/005 345/168 |
| 2014/0121524 A1* | 5/2014 | Chiang et al. ................ 600/459 |
| 2014/0177909 A1* | 6/2014 | Lin et al. ...................... 382/103 |
| 2014/0237432 A1* | 8/2014 | Geurts et al. ................. 715/863 |
| 2014/0320408 A1* | 10/2014 | Zagorsek et al. ............. 345/158 |
| 2015/0035750 A1* | 2/2015 | Bailey et al. ................. 345/158 |
| 2015/0049083 A1* | 2/2015 | Bidne et al. ................. 345/420 |

\* cited by examiner

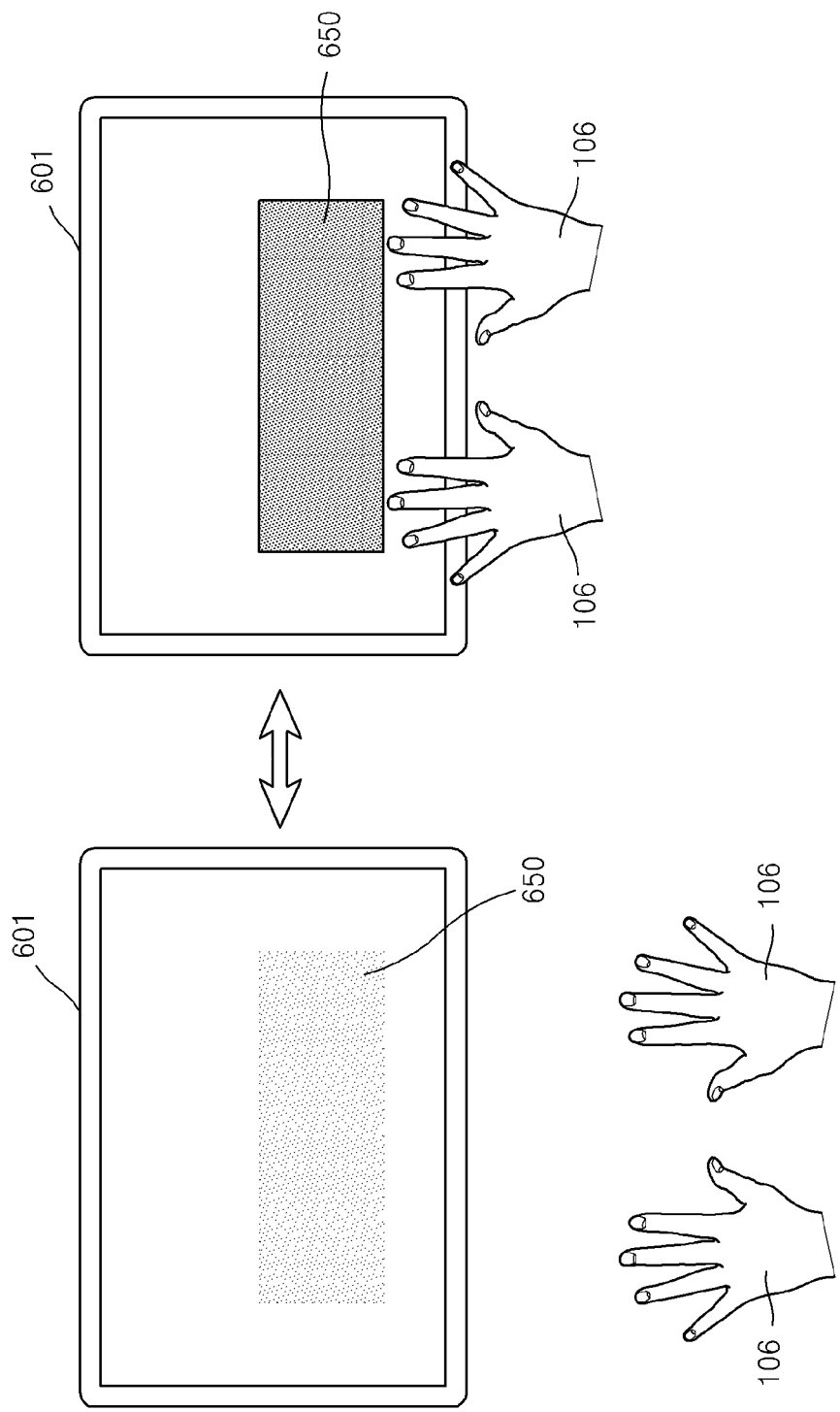

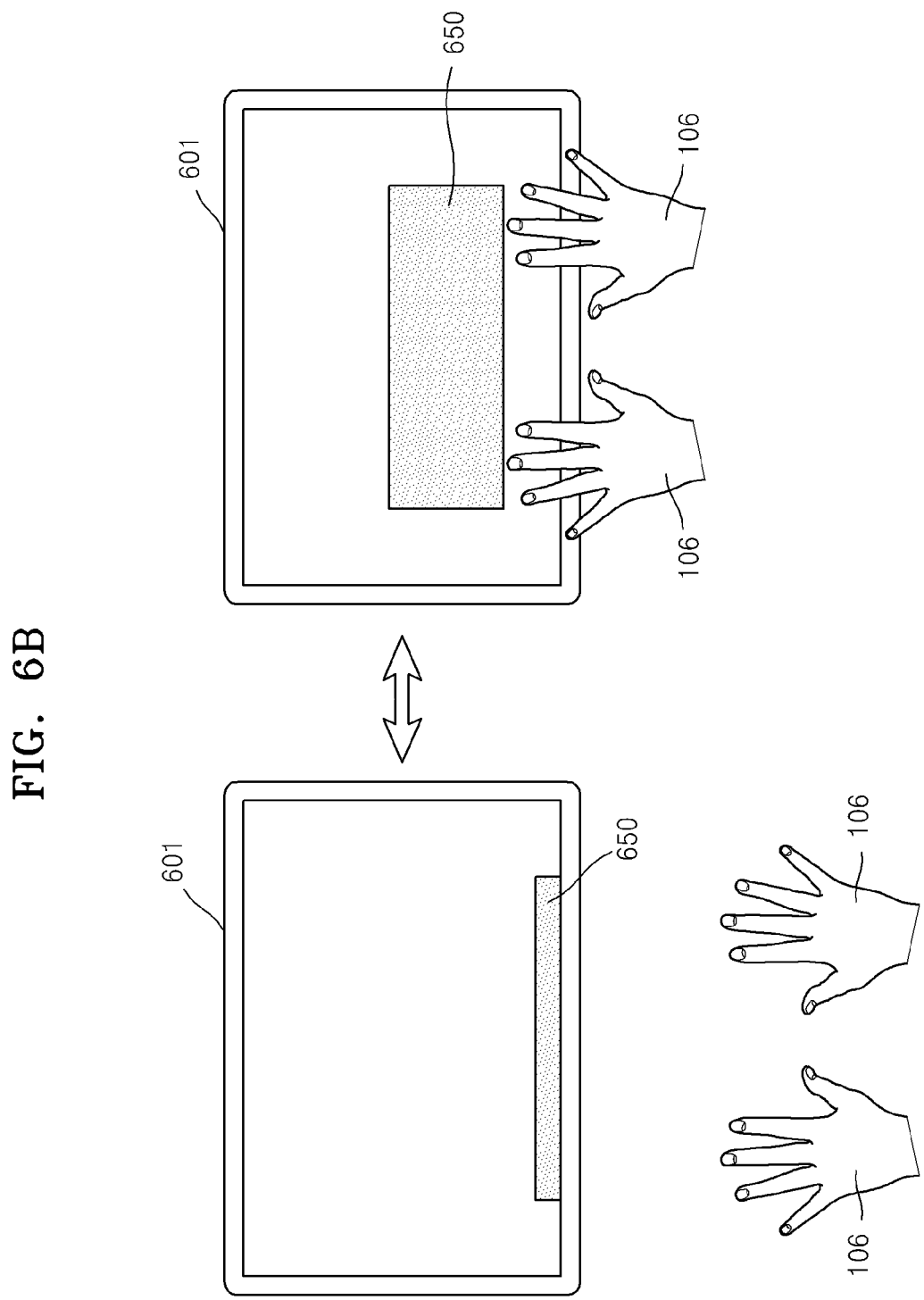

METHOD AND APPARATUS FOR PROVIDING USER INTERFACE FOR MEDICAL DIAGNOSTIC APPARATUS

RELATED APPLICATIONS

This application claims the benefit of Korean Patent Application No. 10-2013-0100580, filed on Aug. 23, 2013, in the Korean Intellectual Property Office, the disclosure of which is incorporated herein in its entirety by reference.

BACKGROUND

1. Field

One or more embodiments of the present invention relate to a method and apparatus for providing user interface of medical diagnostic apparatus, and more particularly, to a method and apparatus that provide a user interface on the basis of a user's gesture.

2. Description of the Related Art

A medical diagnostic system acquires medical image data of an object and displays a medical image generated from the acquired medical image data on a screen to provide the medical image to a user. The medical diagnostic system includes a medical image capturing apparatus and a medical diagnostic apparatus.

The medical image capturing apparatus transmits a signal to an object, and acquires medical image data about a body part, blood flow, or the like of the object by using a signal received from the object in response to the transmitted signal.

For example, the medical image capturing apparatus may acquire ultrasonic image data, X-ray image data, computerized tomography (CT) image data, magnetic resonance (MR) image data, position emission tomography (PET) image data, and other image data.

The medical diagnostic apparatus generates a medical image by using the medical image data acquired from the medical image capturing apparatus, and displays the generated medical image on a screen to provide the medical image to a user. The medical diagnostic apparatus may include a control panel that controls the medical diagnostic system, and is used to set various functions.

Generally, the control panel of the medical diagnostic apparatus includes a plurality of function keys for receiving a user input and an input device such as a keyboard. For example, the keyboard of the medical diagnostic apparatus may be disposed at a top or bottom of the control panel. However, when the input device is fixed to or movably disposed at the top or bottom of the control panel, the usability of the control panel is reduced due to the limited space for mounting it.

Therefore, in order to increase the usability of the control panel, a touch input pad instead of various kinds of input devices may be provided in the control panel. The touch input pad may provide a touch input user interface (UI) that performs functions of various input devices such as a function key and a keyboard, and receive a user input through the touch input UI.

However, in order to select a desired touch input UI through the touch input pad and perform a desired function, a user needs to perform various operations and access many layers of the touch input UI.

Accordingly, medical diagnostic apparatuses that have a control panel with increased usability so that a user is quickly and conveniently provided with a desired UI are needed.

SUMMARY

One or more embodiments of the present invention include a UI providing method and apparatus that provides a UI for a medical diagnostic apparatus on the basis of a user's gesture.

Additional aspects will be set forth in part in the description which follows and, in part, will be apparent from the description, or may be learned by practice of the presented embodiments.

According to one or more embodiments of the present invention, a user interface (UI) providing method for use in a medical diagnostic apparatus includes: detecting a gesture of a hand of a user; determining a touch input UI that corresponds to the detected gesture and is displayed on a screen; and adjusting and displaying the touch input UI on a basis of a distance from the screen to the hand.

The adjusting and displaying of the touch input UI may include changing at least one of transparency, size, and position of the touch input UI on a basis of the distance from the screen to the hand.

The adjusting and displaying of the touch input UI may include, as the distance from the screen to the hand becomes shorter, decreasing the transparency of the touch input UI.

The adjusting and displaying of the touch input UI may include: when the distance from the screen to the hand is equal to a first distance, displaying a portion of the touch input UI on the screen; and when the distance from the screen to the hand is equal to a second distance, displaying an entirety of the touch input UI on the screen, the second distance being shorter than the first distance.

The adjusting and displaying of the touch input UI may include changing at least one of a shape, color, brightness, and flickering period of the touch input UI on a basis of the distance from the screen to the hand.

The detecting of a gesture may include: acquiring an image of the hand; detecting a change in at least one of a palm, knuckle, and fingertip of the hand from the acquired image; and searching for a gesture, corresponding to the detected change in the at least one of the palm, knuckle, and fingertip of the hand, from stored information about at least one gesture.

The adjusting and displaying of the touch input UI may include: detecting a position of the hand; and displaying the touch input UI on a region of the screen corresponding to the detected position.

The touch input UI may include at least one of a virtual keyboard, a time gain compensation (TGC) adjustment UI, a menu selection UI, and an image control UI that controls a rotation of a 3D medical image.

The detecting of a gesture may include detecting a number of hands and a number of fingers, and the determining of a touch input UI may include: when the number of the detected hands is two and the number of the detected fingers is eight or more, determining a virtual keyboard as the touch input UI; when the number of the detected hands is one and the number of the detected fingers is two, determining a TGC adjustment UI as the touch input UI; when the number of the detected hands is one and the number of the detected fingers is one, determining a menu selection UI as the touch input UI; and when the number of the detected hands is one and no finger is detected, determining an image control UI as the touch input UI.

When the touch input UI is a virtual keyboard, the adjusting and displaying of the touch input UI may include: detecting an interval between fingertips of the hand; and displaying the virtual keyboard having a key interval corresponding to the detected interval.

According to one or more embodiments of the present invention, a UI providing apparatus for use in a medical diagnostic apparatus includes: a detector that detects a gesture of a hand of a user; a controller that determines a touch input UI which corresponds to the detected gesture and is displayed on a screen, and adjusts the touch input UI on a basis of a distance from the screen to the hand; and a display that displays the adjusted touch input UI.

The controller may change at least one of transparency, size, and position of the touch input UI on a basis of the distance from the screen to the hand.

As the distance from the screen to the hand becomes shorter, the controller may decrease the transparency of the touch input UI.

When the distance from the screen to the hand is equal to a first distance, the controller may display a portion of the touch input UI on the screen. When the distance from the screen to the hand is equal to a second distance, the controller may display an entirety of the touch input UI on the screen. The second distance may be shorter than the first distance.

The controller may change at least one of a shape, color, brightness, and flickering period of the touch input UI on a basis of the distance from the screen to the hand.

The detector may include: an image acquirer that acquires an image of the hand; an image analyzer that detects a change in at least one of a palm, knuckle, and fingertip of the hand from the acquired image; and a searcher that searches for a gesture, corresponding to the detected change in the at least one of the palm, knuckle, and fingertip of the hand, from stored information about at least one gesture.

The detector may detect a position of the hand, and the controller may control the UI display to display the touch input UI on a region of the screen corresponding to the detected position.

The touch input UI may include at least one of a virtual keyboard, a TGC adjustment UI, a menu selection UI, and an image control UI that controls a rotation of a 3D medical image.

The detector may detect a number of hands and a number of fingers. When the number of the detected hands is two and the number of the detected fingers is eight or more, the controller may determine a virtual keyboard as the touch input UI. When the number of the detected hands is one and the number of the detected fingers is two, the controller may determine a TGC adjustment UI as the touch input UI. When the number of the detected hands is one and the number of the detected fingers is one, the controller may determine a menu selection UI as the touch input UI. When the number of the detected hands is one and no finger is detected, the controller may determine an image control UI as the touch input UI.

When the touch input UI is a virtual keyboard, the detector may detect an interval between fingertips of the hand, and the controller may control the UI display to display the virtual keyboard having a key interval corresponding to the detected interval.

According to one or more embodiments of the present invention, a non-transitory computer-readable storage medium storing a program for executing a UI providing method of a medical diagnostic apparatus, the UI providing method including: detecting a gesture of a hand of a user; determining a touch input UI that corresponds to the detected gesture and is displayed on a screen; and adjusting and displaying the touch input UI on a basis of a distance from the screen to the hand.

BRIEF DESCRIPTION OF THE DRAWINGS

These and/or other aspects will become apparent and more readily appreciated from the following description of the embodiments, taken in conjunction with the accompanying drawings of which:

FIGS. 6A to 6C illustrate an example of a touch input UI providing screen of the UI providing apparatus according to an embodiment of the present invention;

DETAILED DESCRIPTION

Figure 1A:
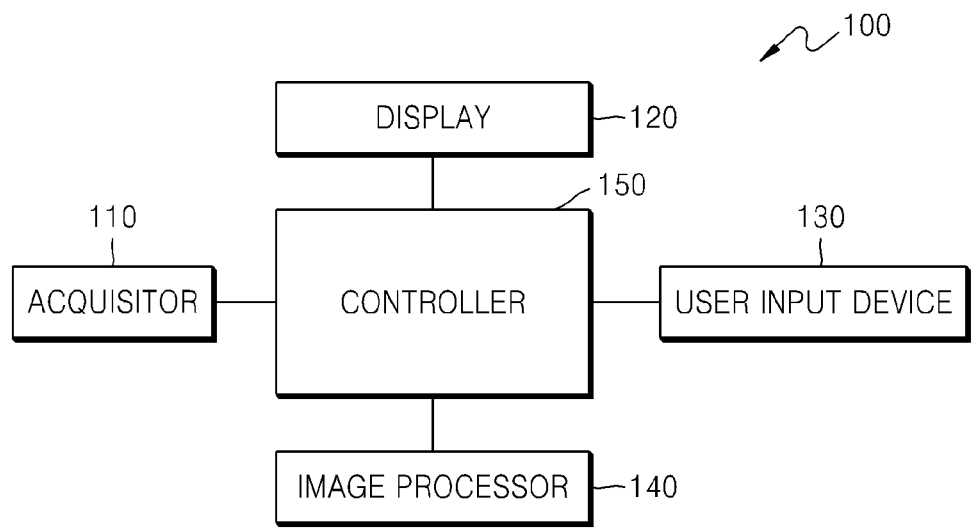
FIGS. 1A and 1B are block diagrams for describing a general medical diagnostic apparatus.

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

The terms used in the present invention are general terms widely used at present, and use thereof has been selected in consideration of the functions of the present invention. However, these terms may be altered according to the intent of an operator skilled in the art, conventional practice, or introduction of new technology. Also, in the case of a term arbitrarily selected by the applicant in a specific case, the meaning of the term will be described in detail in a corresponding description portion of the present invention. Therefore, the terms should be defined on the basis of the entire content of this specification instead of a simple name of each of the terms.

In this disclosure below, when one part (or element, device, etc.) is referred to as being 'connected' to another part (or element, device, etc.), it should be understood that the former can be 'directly connected' to the latter, or 'electrically connected' to the latter via an intervening part (or element, device, etc.). Furthermore, when it is described that one comprises (or includes or has) some elements, it should be understood that it may comprise (or include or has) only those elements, or it may comprise (or include or have) other elements as well as those elements if there is no specific limitation.

Moreover, each of terms " . . . unit", " . . . apparatus" and "module" described in specification denotes an element for performing at least one function or operation, and may be implemented in hardware, software or the combination of hardware and software.

The term "medical image" used herein denotes an image of an object which is acquired from a certain signal. The medical image may be an ultrasonic image, an X-ray image, a computerized tomography (CT) image, a magnetic resonance (MR) image, a position emission tomography (PET) image, or other image acquired by capturing the object, but the present invention is not limited thereto.

The term "object" used herein may be a person, an animal, a part of a person, or a part of an animal. For example, an object may be an organ such as a liver, a heart, a womb, a brain, breasts, an abdomen, or the like, or a blood vessel, but is not limited thereto.

Moreover, the term "user" used herein is a medical expert, and may be a doctor, a nurse, a medical technologist, a medical image expert, or the like, or may be an engineer repairing a medical apparatus. However, the user is not limited thereto.

Exemplary embodiments of the present invention that can be easily embodied by those skilled in the art will now be described in detail with reference to the accompanying drawings. The present invention may, however, be embodied in many different forms and should not be construed as being limited to the embodiments set forth herein. In the accompanying drawings, a portion irrelevant to a description of the present invention will be omitted for clarity.

FIG. 1 shows block diagrams for describing a general medical diagnostic apparatus 100.

The medical diagnostic apparatus 100 may be an apparatus that acquires medical image data from an object, generates a medical image by using the acquired medical image data, and provides the generated medical image to a user.

The medical diagnostic apparatus 100 may be implemented in various ways. For example, the medical diagnostic apparatus 100 described herein may be a mobile terminal that may be connected to a fixed terminal. Examples of the mobile terminal may include a laptop computer, a personal digital assistant (PDA), a tablet personal computer (PC), etc.

As illustrated in FIG. 1A, the medical diagnostic apparatus 100 may include an acquisitor 110, a display 120, a user input device 130, an image processor 140, and a controller 150.

The acquisitor 110 may acquire medical image data from an object. The medical image data may be, for example, two-dimensional (2D) image data or three-dimensional (3D) image data.

The acquisitor 110 may include a medical image capturing apparatus that transmit a certain signal to an object, receive a signal reflected from the object or a signal passing through the object, and acquires medical image data on the basis of the received signal.

The display 120 may display information obtained through processing by the medical diagnostic apparatus 100. For example, the display 120 may display an ultrasonic image of an object and a UI or a content-associated graphical user interface (GUI).

The user input device 130 may be a device for inputting data to be used by a user to control the medical diagnostic apparatus 100. For example, the user input device 130 may include a keypad, a dome switch, a touch pad (for example, of a contact capacitive type, a press resistive type, an infrared sensing type, a surface ultrasonic conductive type, an integration tension measurement type, or a piezo effect type), a jog wheel, and a jog switch, but is not limited thereto.

The image processor 140 may generate a medical image by using medical image data acquired by the acquisitor 110. The image processor 140 may apply various setting values, which are set by a user, to the medical image data. That is, the image processor 140 may apply the various setting values to the medical image data to generate or change the medical image which is displayed on a screen.

The controller 150 controls an overall operation of the medical diagnostic apparatus 100. That is, the controller 150 may overall control the acquisitor 110, the display 120, the user input device 130, and the image processor 140.

Figure 1B:
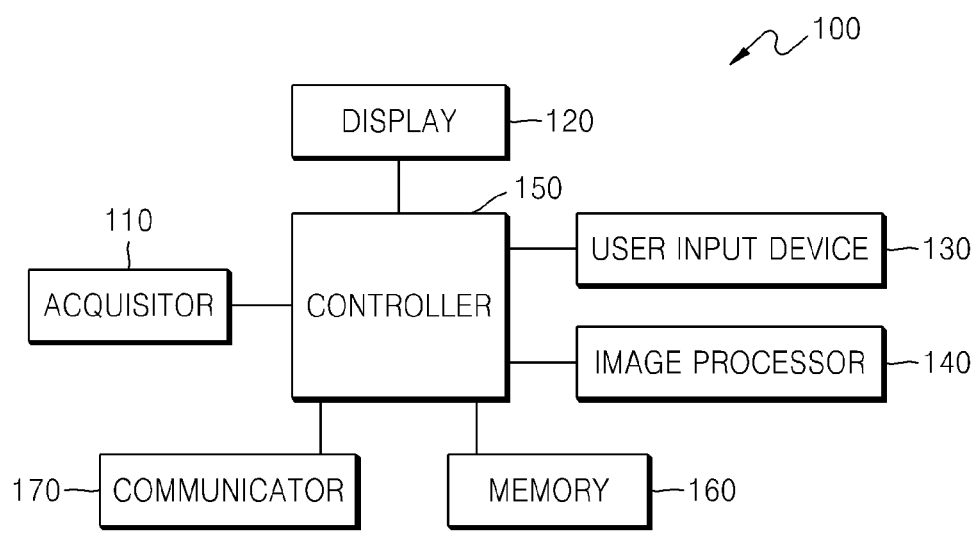

As illustrated in FIG. 1B, the medical diagnostic apparatus 100 may further include a memory 160 and a communicator 170.

The memory 160 may store a program for processing and control by the controller 150, and store input/output data (for example, a predetermined gain value, a medical image, examinee information, probe information, application information, a body marker, etc.).

The memory 160 may include at least one type of a storage medium such as a flash memory, a hard disk, a multimedia micro card, a card type memory (a secure digital (SD) card, an extreme digital (XD) card, or the like), random access memory (RAM), static random access memory (SRAM), read-only memory (ROM), an electrically erasable programmable read-only memory (EEPROM), and a programmable read-only memory (PROM). Also, the medical diagnostic apparatus 100 may operate a web storage or a cloud server which performs a storage function of the memory 160 on the Internet.

The communicator 170 may include one or more element enabling communication between the medical diagnostic apparatus 100 and an external device. For example, the communicator 170 may include a short-distance communication module, a mobile communication module, a wireless Internet module, a wired Internet module, etc.

The short-distance communication module denotes a module for short-distance communication. Short-distance communication technology may include wireless LAN, Wi-Fi, Bluetooth, Bluetooth low energy (BLE), ultra wideband (UWB), near field communication (NFC), Zigbee, Wi-Fi direct (WFD), and infrared data association (IrDA), but the short-distance communication technology is not limited thereto.

The mobile communication module transmits/receives a radio frequency (RF) signal to/from at least one of a base station, an external terminal, and a server over a mobile communication network. The wireless Internet module denotes a module for wirelessly accessing the Internet, and may be built into or provided outside the medical diagnostic apparatus 100. The wired Internet module denotes a module for accessing the Internet in a wired manner.

The communicator 170 may transmit the generated medical image to an external device through wired/wireless communication. Examples of the external device according to an embodiment of the present invention may include a smartphone, a laptop computer, a tablet PC, an e-book terminal, a digital broadcasting terminal, a PDA, a portable multimedia player (PMP), a digital camera, etc., but is not limited thereto.

The user input device 130 of the medical diagnostic apparatus 100 of FIG. 1 is provided outside the medical diagnostic apparatus 100. The user input device 130 receives a user input. Due to a spatial limitation of the medical diagnostic apparatus 100, an area of the medical diagnostic apparatus 100 occupied by the user input device 130 is limited.

Therefore, a UI providing apparatus according to an embodiment of the present invention increases the usability of the medical diagnostic apparatus 100, by quickly and conveniently providing a UI desired by a user.

The UI providing apparatus according to an embodiment of the present invention may detect a hand gesture of a user located near the medical diagnostic apparatus 100, and may automatically determine a touch input UI to be displayed on a screen on the basis of the detected hand gesture. According to an embodiment of the present invention, a separate selection operation of providing a touch input UI desired by a user is not needed.

Moreover, the UI providing apparatus according to an embodiment of the present invention may analyze a hand approach motion of a user which approaches the medical diagnostic apparatus, and adjust and display at least one of transparency, position, and size of a touch input UI. According to an embodiment of the present invention, when the user does not use the touch input UI, the UI providing apparatus may not display the touch input UI on a screen, or may display the touch input UI so as not to cover the other image displayed on the screen. Therefore, according to an embodiment of the present invention, when the user does not use the touch input UI, the UI providing apparatus prevents the touch input UI from covering the other image displayed on the screen.

A UI providing apparatus 200 according to an embodiment of the present invention, which increases the usability of the medical diagnostic apparatus 100 and quickly and conveniently provides a UI, will be described in detail with reference to FIG. 2.

Figure 2:
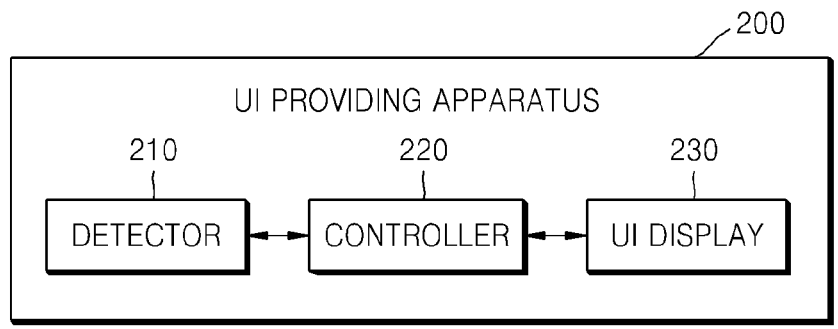
FIG. 2 is a block diagram for describing a UI providing apparatus according to an embodiment of the present invention.

FIG. 2 is a block diagram for describing the UI providing apparatus 200 according to an embodiment of the present invention.

The UI providing apparatus 200 according to an embodiment of the present invention denotes an apparatus that provides a UI to a user by using the medical diagnostic apparatus 100 of FIG. 1.

The UI providing apparatus 200 according to an embodiment of the present invention may be included in or connected to the medical diagnostic apparatus 100 of FIG. 1. For example, the UI providing apparatus 200 of FIG. 2 may be included in the user input device 130 of FIG. 1, but is not limited thereto.

Elements of the UI providing apparatus 200 according to an embodiment of the present invention illustrated in FIG. 2 may be included in at least one element of the medical diagnostic apparatus 100 of FIG. 1, and the UI providing apparatus 200 may perform all or some of the functions of the elements of the medical diagnostic apparatus 100.

Therefore, although not described below, the above-described details of the medical diagnostic apparatus 100 of FIG. 1 may apply to the UI providing apparatus 200 of FIG. 2.

As illustrated in FIG. 2, the UI providing apparatus 200 according to an embodiment of the present invention may include a detector 210, a controller 220, and a UI display 230.

The detector 230 detects a user's hand gesture. The term "gesture" may denote a posture of the user's hand at a certain time, a change in the posture of the user's hand for a certain time, a position change in the user's hand for a certain time, or a motion of the user's hand for a certain time.

The detector 210 may include a camera, which acquires an image, and various sensors. The various sensors included in the detector 210 may include a depth sensor, an infrared sensor, an ultrasonic sensor, and a sensor similar thereto.

The detector 210 may detect a gesture on the basis of an image obtained by capturing a hand or on the basis of a signal (for example, an infrared signal, an ultrasonic signal, etc.) received from the hand.

As an example, the detector 210 may detect a gesture on the basis of an image of a hand. In this case, the detector 210 may acquire the image of the hand, and detect a change in at least one of a palm, knuckle, and fingertip of the hand from the acquired image.

As another example, the detector 210 may detect a gesture on the basis of a certain signal received from a hand. In this case, the detector 210 may transmit the certain signal to the hand, and detect the gesture on the basis of a signal which is received from the hand in response to the transmitted signal. For example, the certain signal may be an infrared signal or an ultrasonic signal.

The detector 210 may detect a change in at least one of the palm, knuckle, and fingertip of the hand from a certain signal received from an object.

The detector 210 may search for a gesture, which corresponds to the detected change in at least one of the palm, knuckle, and fingertip of the hand, from stored information about at least one gesture.

Moreover, the detector 210 may further detect a distance from a screen of the UI display 230 to the hand of which the gesture has been detected. The distance from the screen to the hand may denote, for example, the shortest straight distance from the screen to the closest fingertip. The distance from the screen to the hand may be calculated by analyzing the image of the hand or analyzing a position of the hand which is detected by a sensor.

The controller 220 determines a touch input UI which corresponds to the gesture detected by the detector 210 and is displayed on a screen of the UI display 230.

The term "touch input UI" denotes a GUI that receives a user's touch input. For example, the touch input UI may receive at least one of an input of a setting value necessary to acquire and process medical image data, an input for controlling the UI providing apparatus 200 and an apparatus connected to the UI providing apparatus 200, an input for setting a function of each of the UI providing apparatus 200 and the apparatus connected to the UI providing apparatus 200, and an input of a text written by the user.

The controller 220 adjusts the touch input UI which is determined based on the distance from the screen to the hand of which the gesture has been detected.

Moreover, the controller 220 may control an overall operation of the UI providing apparatus 200, and control the detector 210 and the UI display 230 so as to perform a UI providing method according to an embodiment of the present invention.

The UI display 230 displays the touch input UI, adjusted by the controller 220, on a screen.

Moreover, the UI display 230 may further display a medical image. Also, the UI display 230 may display information obtained through processing by the UI providing apparatus 200. For example, the UI display 230 may display state information, which is necessary to adjust and display the touch input UI determined based on the hand gesture, and a UI or a GUI associated with a setting of a function.

The UI display 230 may include at least one of a liquid crystal display (LCD), a thin film transistor-liquid crystal display, an organic light-emitting diode (OLED) display, a flexible display, a 3D display, and an electrophoretic display. The UI providing apparatus 200 may include two or more UI displays 230 depending on an implementation type of the UI providing apparatus 200.

The UI display 230 may be used as an input device that receives a user input through the touch input UI, in addition to an output device that displays the touch input UI.

For example, the UI display 120 may include a touch screen in which a display panel and a touch pad form a layer structure. The touch pad may receive a touch input by using various types such as a contact capacitive type, a press resistive type, an infrared sensing type, a surface ultrasonic conductive type, an integration tension measurement type, and a piezo effect type.

The term "touch input" used herein may denote an input by a proximity touch as well as a real touch. The term "real touch" denotes a case in which a pointer actually touches a screen, and the term "proximity touch" denotes a case in which the pointer does not actually touch the screen but reaches a position separated from the screen by a certain distance.

The term "pointer" denotes a part of a user body or a touch instrument for really touching or proximity-touching a specific portion of a displayed screen. Examples of the pointer include an electronic pen, a finger, etc.

Various sensors may be provided inside or near a touch screen, for detecting a touch input. An example of a sensor for sensing a touch of the touch screen is a tactile sensor. The tactile sensor denotes a sensor that senses a touch by a specific object by a degree, in which a user feels, or more. The tactile sensor may sense various pieces of information such as a roughness of a touched surface, a stiffness of a touched object, a temperature of a touched point, etc.

Moreover, an example of a sensor for sensing a touch of the touch screen is a proximity sensor. The proximity sensor denotes a sensor that detects an object approaching a detection surface or an object near the detection surface by using an electromagnetic force or infrared light without any mechanical contact. Examples of the proximity sensor include a transmissive photosensor, a directly reflective photosensor, a mirror reflective photosensor, a high frequency oscillation-type proximity sensor, a capacitive proximity sensor, a magnetic proximity sensor, and an infrared proximity sensor.

Examples of a user's touch gesture may include a tap, a touch and hold, a double tap, a drag, a panning, a flick, a drag and drop, and a swipe.

Hereinafter, a method in which the UI providing apparatus 200 according to an embodiment of the present invention provides a UI will be described in detail with reference to FIG. 3.

Figure 3:
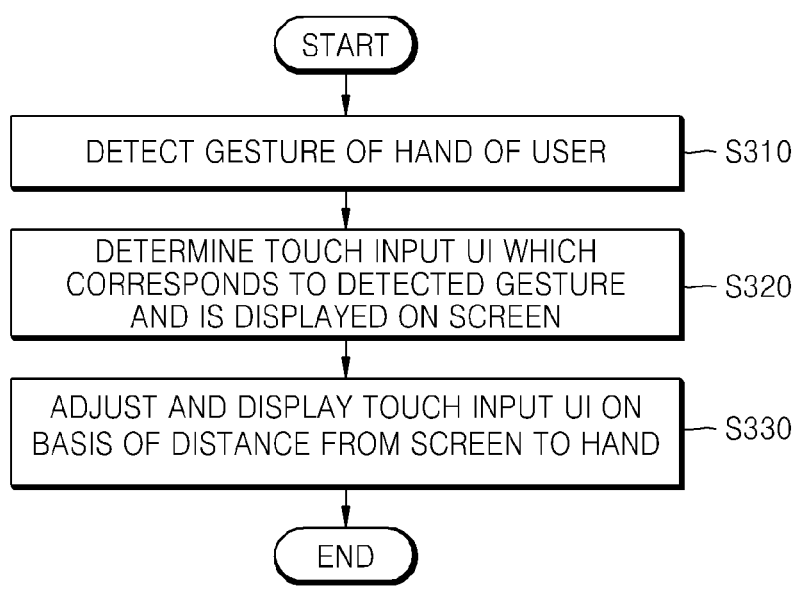
FIG. 3 is a flowchart for describing a UI providing method according to an embodiment of the present invention.

FIG. 3 is a flowchart for describing a UI providing method according to an embodiment of the present invention.

In operation S310, the UI providing apparatus 200 according to an embodiment of the present invention detects a user's hand gesture.

The UI providing apparatus 200 may detect the hand gesture on the basis of an image obtained by capturing the hand with a camera and a signal received from the hand by using a sensor.

As an example, the UI providing apparatus 200 may acquire an image of the hand which is located within a certain distance from a screen by using the camera, and detect a change in at least one of a palm, knuckle, and fingertip of the hand from the acquired image. The certain distance to the screen may be a distance that is previously stored or is input by the user.

The UI providing apparatus 200 may estimate a region corresponding to the hand from the acquired image, and detect the number of hands or the number of fingers on the basis of the estimated region corresponding to the hand.

As another example, the UI providing apparatus 200 may acquire a signal for the hand located within the certain distance from the screen by using the sensor, and detect a change in at least one of the palm, knuckle, and fingertip of the hand on the basis of the acquired image.

The UI providing apparatus 200 may estimate the region corresponding to the hand from the received signal, and detect the number of hands or the number of fingers on the basis of the estimated region corresponding to the hand.

The UI providing apparatus 200 may previously store information about at least one gesture. The UI providing apparatus 200 may store, as information about a gesture, information about the change in at least one of the palm, knuckle, and fingertip of the hand.

Therefore, the UI providing apparatus 200 may search for a gesture corresponding to the detected change in at least one of the palm, knuckle, and fingertip of the hand from the stored information about the at least one gesture.

A method of detecting a hand gesture is not limited to the above-described method, and it is obvious to those skilled in the art that various methods in addition to the above-described method may be used.

In operation S320, the UI providing apparatus 200 according to an embodiment of the present invention determines a touch input UI which corresponds to the gesture (which is detected in operation S310) and is displayed on a screen.

The UI providing apparatus 200 may previously store a certain gesture and at least one touch input UI corresponding to the certain gesture, wherein the certain gesture and the at least one touch input UI are mapped to each other. The UI providing apparatus 200 may search for a touch input UI corresponding to the detected gesture from the stored at least one touch input UI.

Examples of the touch input UI may include at least one of a virtual keyboard, a time gain compensation (TGC) adjustment UI, a menu selection UI, and an image control UI that controls a rotation of a 3D medical image.

For example, the UI providing apparatus 200 may determine a touch input UI to be displayed on a screen, on the basis of a number of hands and a number of fingers which are detected in operation S310.

As an example, when the number of the detected hands is two and the number of the detected fingers is eight or more than eight, the UI providing apparatus 200 may determine the virtual keyboard as the touch input UI to be displayed on the screen.

Moreover, when the number of the detected hands is one and the number of the detected fingers is two, the UI providing apparatus 200 may determine the TGC adjustment UI as the touch input UI to be displayed on the screen.

Moreover, when the number of the detected hands is one and the number of the detected fingers is one, the UI providing apparatus 200 may determine the menu selection UI as the touch input UI to be displayed on the screen.

Moreover, when the number of the detected hands is one and no finger is detected, the UI providing apparatus 200 may determine the image control UI as the touch input UI to be displayed on the screen.

The touch input UI determined based on the number of detected hands and the number of detected fingers will be described below in detail with reference to FIG. 7.

In operation S330, the UI providing apparatus 200 according to an embodiment of the present invention adjusts and displays the touch input UI which is determined in operation S320, on the basis of a distance from a screen to a hand.

For example, the UI providing apparatus 200 may change at least one of transparency, size, position, shape, color, brightness, and flickering period of the touch input UI on the basis of the distance from the screen to the hand.

According to an embodiment of the present invention, as the distance from the screen to the hand becomes shorter, the UI providing apparatus 200 may decrease the transparency of the touch input UI. That is, as the user's hand is closer to the screen, the UI providing apparatus 200 according to the current embodiment of the present invention may display the touch input UI on the screen in order for the touch input UI to be clearly differentiated from a peripheral region of the screen.

According to other embodiment of the present invention, as the distance from the screen to the hand becomes shorter, the UI providing apparatus 200 may change a position of the touch input UI, displayed on the screen, from a peripheral region to a central region of the screen.

When the distance from the screen to the hand is equal to a first distance, the UI providing apparatus 200 according to the current embodiment of the present invention may display a portion of the touch input UI on the screen. When the distance from the screen to the hand is equal to a second distance shorter than the first distance, the UI providing apparatus 200 may display an entirety of the touch input UI on the screen.

That is, as the user's hand is closer to the screen, the UI providing apparatus 200 according to the second embodiment of the present invention may change a position of the touch input UI to a position which enables the user to easily used the touch input UI.

According to other embodiment of the present invention, as the distance from the screen to the hand becomes shorter, the UI providing apparatus 200 may increase a size of the touch input UI. That is, as the user's hand is closer to the screen, the UI providing apparatus 200 according to the current embodiment of the present invention may increase the size of the touch input UI to a size which enables the user to easily used the touch input UI.

The above-described first to third embodiments of the present invention will be described below in detail with reference to FIG. 6.

The UI providing apparatus 200 according to an embodiment of the present invention may detect a position of a hand, and display a touch input UI on a region of a screen corresponding to the detected position of the hand.

Moreover, the UI providing apparatus 200 according to an embodiment of the present invention may detect a size or posture of the hand, and manipulate and display the touch input UI in correspondence with the detected size or posture of the hand. For example, when the touch input UI determined in operation S320 is the virtual keyboard, the UI providing apparatus 200 may detect an interval between fingertips, and display the virtual keyboard so as to have a key interval corresponding to the detected interval.

The virtual keyboard, which is adjusted so as to have the key interval corresponding to the detected interval between the fingertips, will be described below in detail with reference to FIG. 8.

Figure 4:
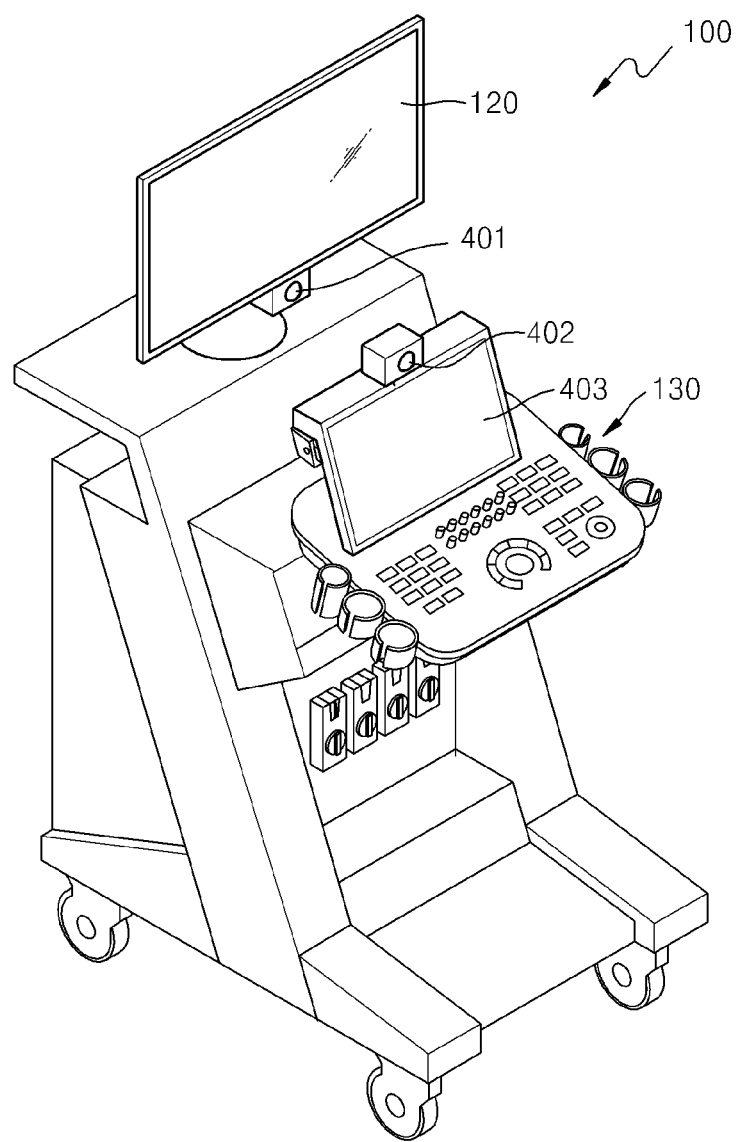
FIG. 4 is a diagram for describing a method in which the UI providing apparatus according to an embodiment of the present invention provides a UI for a medical diagnostic apparatus.

FIG. 4 is a diagram for describing a method in which the UI providing apparatus according to an embodiment of the present invention provides a UI for a medical diagnostic apparatus.

As illustrated in FIG. 4, the medical diagnostic apparatus 100 may include the display 120 that displays a medical image and the user input device 130 that receives an input for controlling the medical diagnostic apparatus 100 from a user.

The UI providing apparatus 200 according to an embodiment of the present invention may include the medical diagnostic apparatus 100 of FIG. 4.

For example, the detector 210 of the UI providing apparatus 200 may be disposed in a lower region 401 under the display 120 of the medical diagnostic apparatus 100, or may be disposed in an upper region 402 on a touch pad 403 of the user input device 130 of the medical diagnostic apparatus 100.

When the display 120 or touch pad 403 of the medical diagnostic apparatus 100 displays a certain image on a screen and simultaneously acquires an image of a hand in front of the screen, the detector 210 of the UI providing apparatus 200 may be included in the display 120 or touch pad 403 of the medical diagnostic apparatus 100.

The detector 210 of the UI providing apparatus 200 may include at least one of a camera, an infrared sensor, and an ultrasonic sensor.

The UI providing apparatus 200 may display a touch input UI, which is determined based on a gesture of the hand detected by the detector 210, on the UI display 230. The UI display 230 of the UI providing apparatus 200 may be included in the display 120 or touch pad 403 of the medical diagnostic apparatus 100.

For example, the UI providing apparatus 200 according to an embodiment of the present invention may display a touch input UI on the touch pad 403 of the medical diagnostic apparatus 100. When a user's hand is closer to the touch pad 403 of the medical diagnostic apparatus 100, the UI providing apparatus 200 may detect a gesture of the hand, and display a touch input UI, which is determined based on the detected gesture, in the touch pad 403.

Therefore, the UI providing apparatus 200 according to an embodiment of the present invention includes only the display 230 that provides various touch input UIs without other various input devices (i.e., a keyboard, various function keys, a TGC adjustment dial, etc.). Thus, the usability and use of space of the medical diagnostic apparatus 100 are increased.

Moreover, by displaying a touch input UI which is determined based on a user's hand gesture, a touch input UI desired by the user is provided quickly and conveniently.

Figure 5:
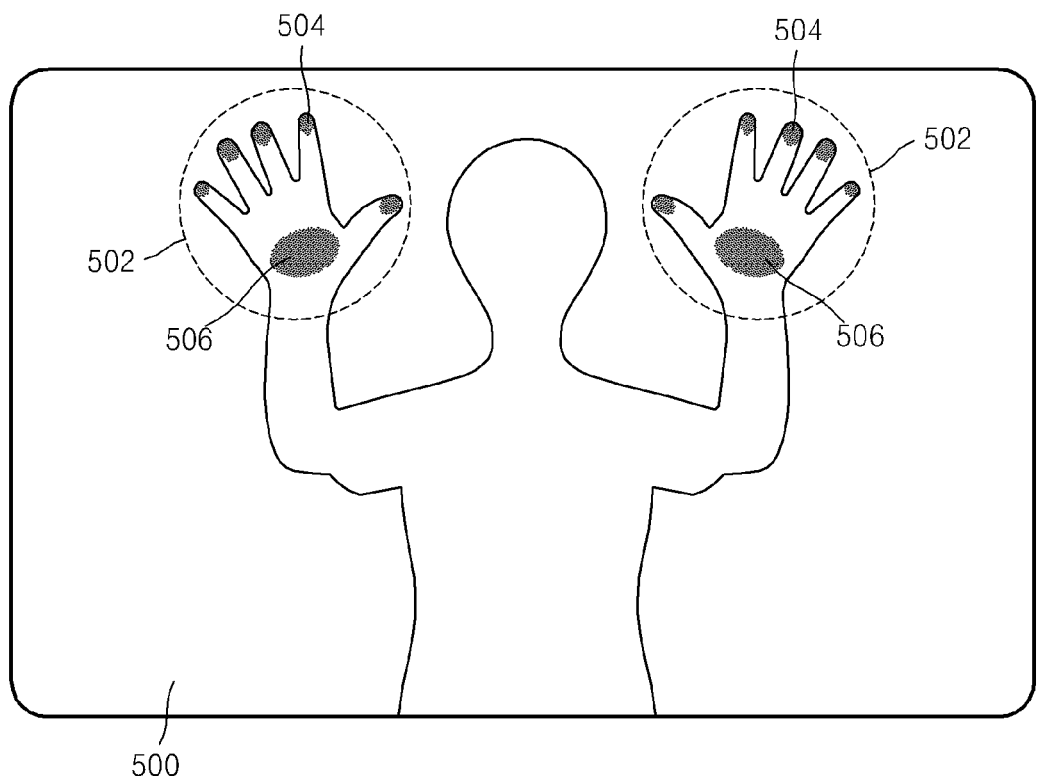
FIG. 5 is a diagram for describing a method of detecting a user's hand gesture according to an embodiment of the present invention.

FIG. 5 is a diagram for describing a method of detecting a user's hand gesture according to an embodiment of the present invention.

As illustrated in FIG. 5, the UI providing apparatus 200 may acquire an image 500 of a hand located within a certain distance from a screen, and detect a change in at least one of a palm, knuckle, and fingertip of the hand from the acquired image.

For example, the UI providing apparatus 200 may estimate a region 502 corresponding to the hand from the acquired image 500. The UI providing apparatus 200 may estimate, on the basis of the estimated region 502 corresponding to the hand, a region 504 corresponding to the fingertip and a region 506 corresponding to the palm.

The UI providing apparatus 200 may detect a gesture of the hand on the basis of a movement (for example, a moving distance or angle) of the region 504 corresponding to the fingertip with respect to the region 506 corresponding to the palm.

For example, when the region 506 corresponding to the palm is closer to the region 504 corresponding to the fingertip, the UI providing apparatus 200 determines a current motion as a motion in which the user curls a finger, and when the region 506 corresponding to the palm is farther away from the region 504 corresponding to the fingertip, the UI providing apparatus 200 determines the current motion as a motion in which the user extends the finger. The UI providing apparatus 200 may detect the hand gesture on the basis of the determined motion of the finger.

A method of detecting a hand gesture is not limited to the above-described method, and it is obvious to those skilled in the art that various methods in addition to the above-described method may be used.

FIG. 6 illustrates an example of a touch input UI providing screen of the UI providing apparatus according to an embodiment of the present invention.

FIG. 6A illustrates an example of a touch input UI providing screen of the UI providing apparatus according to a first embodiment of the present invention.

As illustrated in FIG. 6A, the UI providing apparatus 200 according to the first embodiment of the present invention may change a transparency of a touch input UI on the basis of a distance from a screen 601 of the display 203 to a user's hand 106.

According to the current embodiment of the present invention, as the distance from the screen 601 to the hand 106 becomes shorter, the UI providing apparatus 200 may decrease the transparency of the touch input UI.

That is, as the user's hand 106 is closer to the screen 601, the UI providing apparatus 200 according to the first embodiment of the present invention may opaquely display a touch input UI 650 on the screen 601 in order for the touch input UI 650 to be clearly differentiated from a peripheral region of the screen 601.

Moreover, as the user's hand 106 is farther away from the screen 601, the UI providing apparatus 200 according to the first embodiment of the present invention may increase the transparency of the touch input UI 650.

Therefore, when the user does not desire to input a touch input (i.e., when the user's hand 106 is farther away from the screen 601), the UI providing apparatus 200 may transparently display the touch input UI 650, thus preventing the touch input UI 650 from covering the other image displayed on the screen 601.

FIG. 6B illustrates an example of a touch input UI providing screen of the UI providing apparatus according to other embodiment of the present invention.

As illustrated in FIG. 6B, the UI providing apparatus 200 according to the current embodiment of the present invention may change a position of the touch input UI on the basis of a distance from the screen 601 of the display 203 to the user's hand 106.

In this case, as the distance from the screen 601 to the hand 106 becomes shorter, the UI providing apparatus 200 may change the position of the touch input UI from a peripheral region to a central region of the screen 601 or a region corresponding to a position of the hand.

That is, as the user's hand 106 is closer to the screen 601, the UI providing apparatus 200 according to the current embodiment of the present invention may dispose the touch input UI 650 at a position which enables the user to easily use the touch input UI 650.

Moreover, as the user's hand 106 is farther away from the screen 601, the UI providing apparatus 200 may move the touch input UI to the peripheral region of the screen 601.

Therefore, when the user does not desire to input the touch input (i.e., when the user's hand 106 is farther away from the screen 601), the UI providing apparatus 200 may move the touch input UI to the peripheral region of the screen 601, and allow only a portion of the touch input UI to be displayed on the screen 601, thus preventing the touch input UI 650 from covering the other image displayed on the screen 601.

Figure 6C:
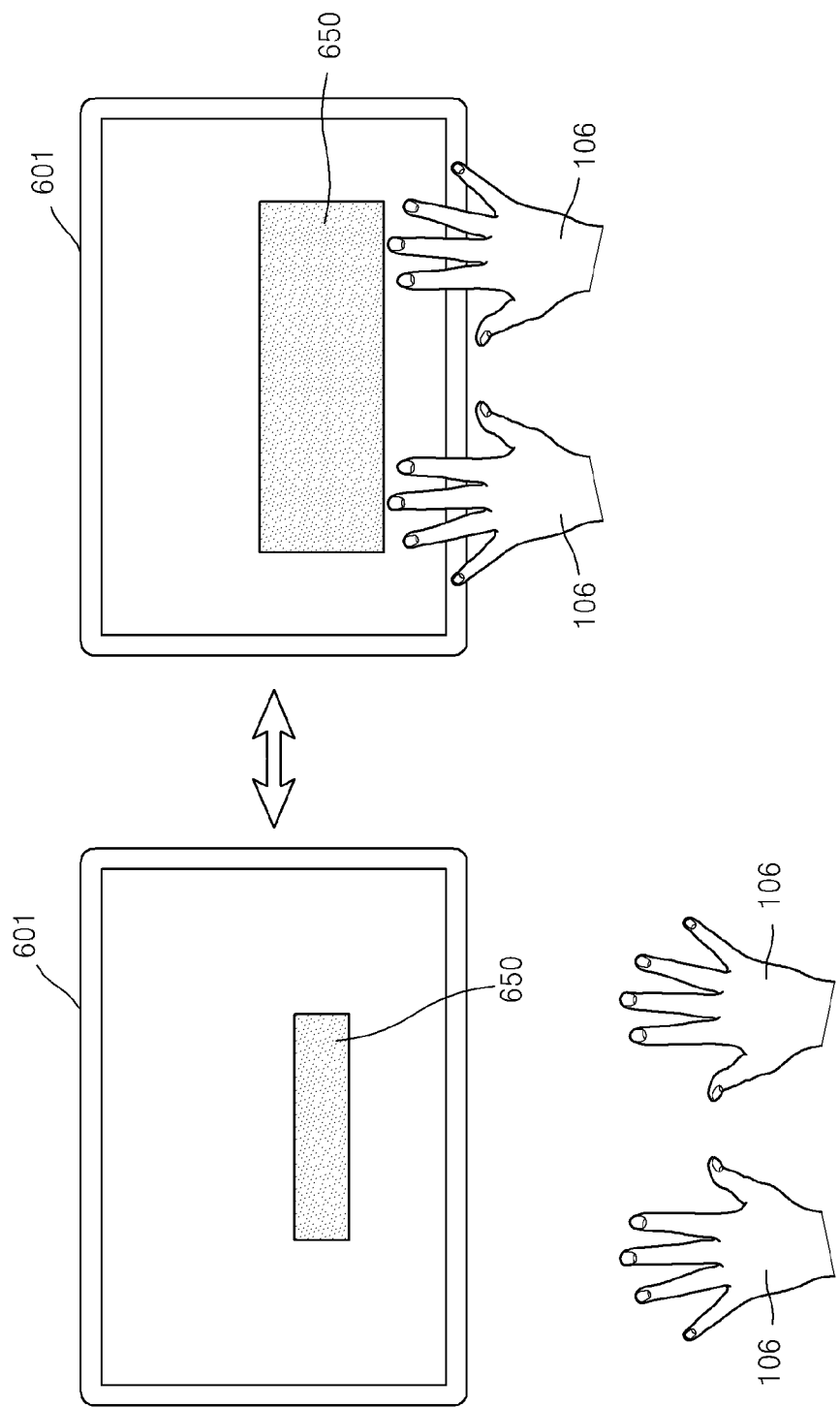

FIG. 6C illustrates an example of a touch input UI providing screen of the UI providing apparatus according to other embodiment of the present invention.

As illustrated in FIG. 6C, the UI providing apparatus 200 according to the current embodiment of the present invention may change a size of the touch input UI on the basis of the distance from the screen 601 of the display 203 to the user's hand 106.

According to the current embodiment, as the distance from the screen 601 to the hand 106 becomes shorter, the UI providing apparatus 200 may increase the size of the touch input UI.

That is, as the user's hand 106 is closer to the screen 601, the UI providing apparatus 200 according to the current embodiment of the present invention may increase the touch input UI 650 to a size which enables the user to easily use the touch input UI 650.

Moreover, as the user's hand 106 is farther away from the screen 601, the UI providing apparatus 200 according to FIG. 6A may decrease the size of the touch input UI 650.

Therefore, when the user does not desire to input the touch input (i.e., when the user's hand 106 is farther away from the screen 601), the UI providing apparatus 200 may adjust the touch input UI 650 to a small size, thus preventing the touch input UI 650 from covering the other image displayed on the screen 601.

As illustrated in FIG. 6, the UI providing apparatus 200 according to the embodiments of FIGS. 6A to 6B may change at least one of the transparency, position, and size of the touch input UI on the basis of the distance from the screen 610 to the user's hand 106.

Therefore, the user using the UI providing apparatus 200 according to the embodiments of FIGS. 6A to 6B may merely move the hand to a position close to the screen 601 to receive the touch input UI 650 of which at least one of the transparency, position, and size has been adjusted in order for the user to easily use the touch input UI 650.

Moreover, when the user does not desire to input the touch input, the user may merely move the hand to a position far away from the screen 601 to receive the touch input UI 650 of which at least one of the transparency, position, and size has been adjusted in order to prevent the touch input UI 650 from covering the other image displayed on the screen 601.

The method in which the UI providing apparatus 200 according to an embodiment of the present invention adjusts a touch input UI on the basis of a distance from a screen to a hand is not limited to the above-described embodiments, and it is obvious to those skilled in the art that a similar method in addition to the above-described embodiments may be used.

FIG. 7 illustrates an example of a touch input provided through the UI providing apparatus according to an embodiment of the present invention.

The UI providing apparatus 200 according to an embodiment of the present invention determines a touch input UI to be displayed on a screen on the basis of a detected hand gesture. The UI providing apparatus 200 may provide a plurality of touch input UIs corresponding to a plurality of input devices.

For example, the UI providing apparatus 200 may display a GUI indicating a keyboard in a touch pad, and receive an input of a text, typewritten by a user, through the displayed GUI. Also, the UI providing apparatus 200 may display a GUI indicating a slide bar which enables a TGC to be adjusted, and receive through the displayed GUI a user input of dragging the slide bar.

As described above, the UI providing apparatus 200 according to an embodiment of the present invention may provide a touch input UI, which include an image indicating an input device and has the same function as that of the input device, through a screen.

At this time, the UI providing apparatus 200 may set a hand gesture as a reference for determining a touch input UI on the basis of hand gestures of the user using various input devices. That is, a hand gesture set as a reference for determining a certain touch input UI may be the same as or similar to a hand gesture of the user using an input device corresponding to the touch input UI.

Figure 7A:
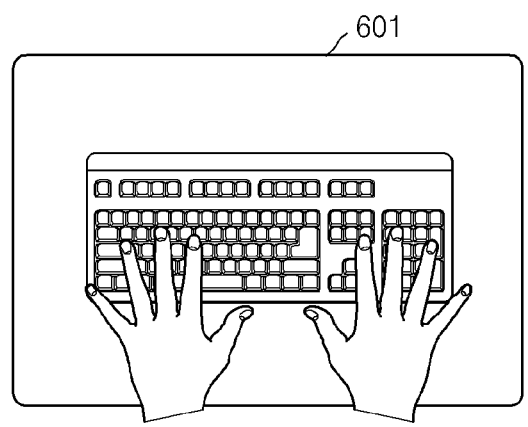
FIGS. 7A to 7D illustrate an example of a touch input provided through the UI providing apparatus according to an embodiment of the present invention.

For example, as illustrated in FIG. 7(a), when a user opens the two hands and makes a gesture similar to using a keyboard, the UI providing apparatus 200 according to an embodiment of the present invention may display a virtual keyboard 701 on a screen 601.

Therefore, when the user's two hands making the gesture of FIG. 7(a) are located within a certain range from the medical diagnostic apparatus 100, the UI providing apparatus 200 may display the virtual keyboard 601 on the screen 601.

The certain range from the medical diagnostic apparatus 100 may denote, for example, a case in which the user's fingertip is located within 30 cm from a top of a control panel of the medical diagnostic apparatus 100.

When only one hand of the user is located within the certain range from the medical diagnostic apparatus 100, the UI providing apparatus 200 allows the virtual keyboard 701 to be no longer displayed on the screen 601.

Figure 7B:
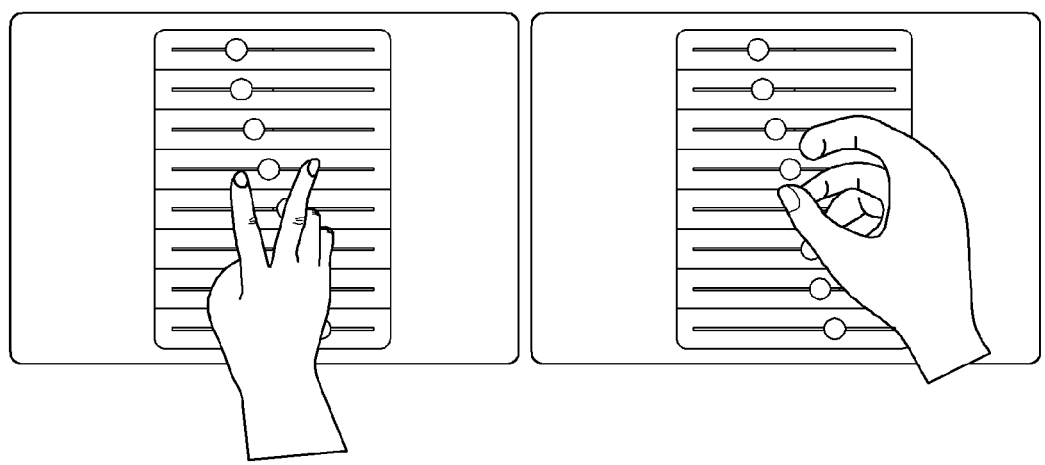

As illustrated in FIG. 7(b), when the user opens the two hands and makes a gesture similar to dragging a slide bar which is used to adjust the TGC, the UI providing apparatus 200 according to an embodiment of the present invention may display a TGC adjustment UI 720 on the screen 601.

Figure 7C:
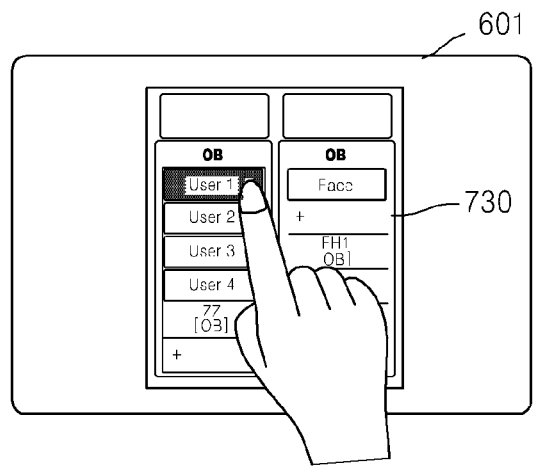

As illustrated in FIG. 7(c), when the user extends one finger and makes a gesture similar to pushing a function key for selecting a certain function, the UI providing apparatus 200 according to an embodiment of the present invention may display a menu selection UI 730 on the screen 601.

Figure 7D:
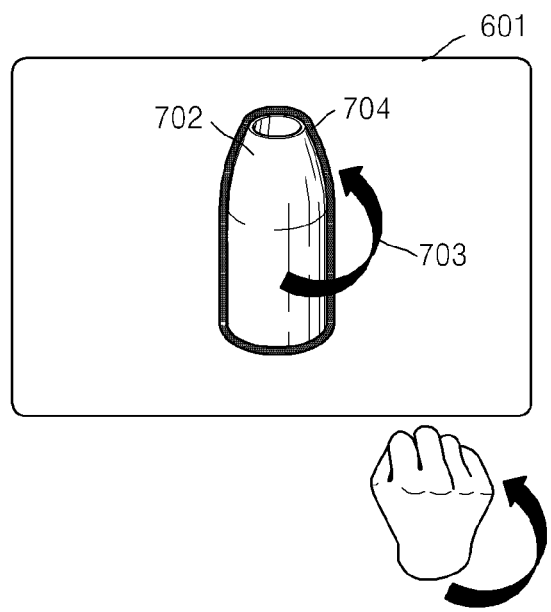

As illustrated in FIG. 7(d), when the user curls five fingers and makes a gesture similar to making a fist, the UI providing apparatus 200 according to an embodiment of the present invention may display an image control UI 740, which is used to control a rotation of a 3D medical image, on the screen 601.

For example, the image control UI 740 may have the form of a border of a 3D image 702 of an object displayed on the screen 601.

The UI providing apparatus 200 according to an embodiment of the present invention may provide the image control UI 740 onto the screen 601 on the basis of the user's detected gesture. The medical diagnostic apparatus 100 may receive an image control input for rotating the user's hand through the provided image control UI 740.

As indicated by an arrow 703 in FIG. 7(d), the medical diagnostic apparatus 100 may receive an input for rotating the user's hand, and rotate the 3D image 702 displayed on the screen 601 in correspondence with the rotation of the hand.

Figure 8:
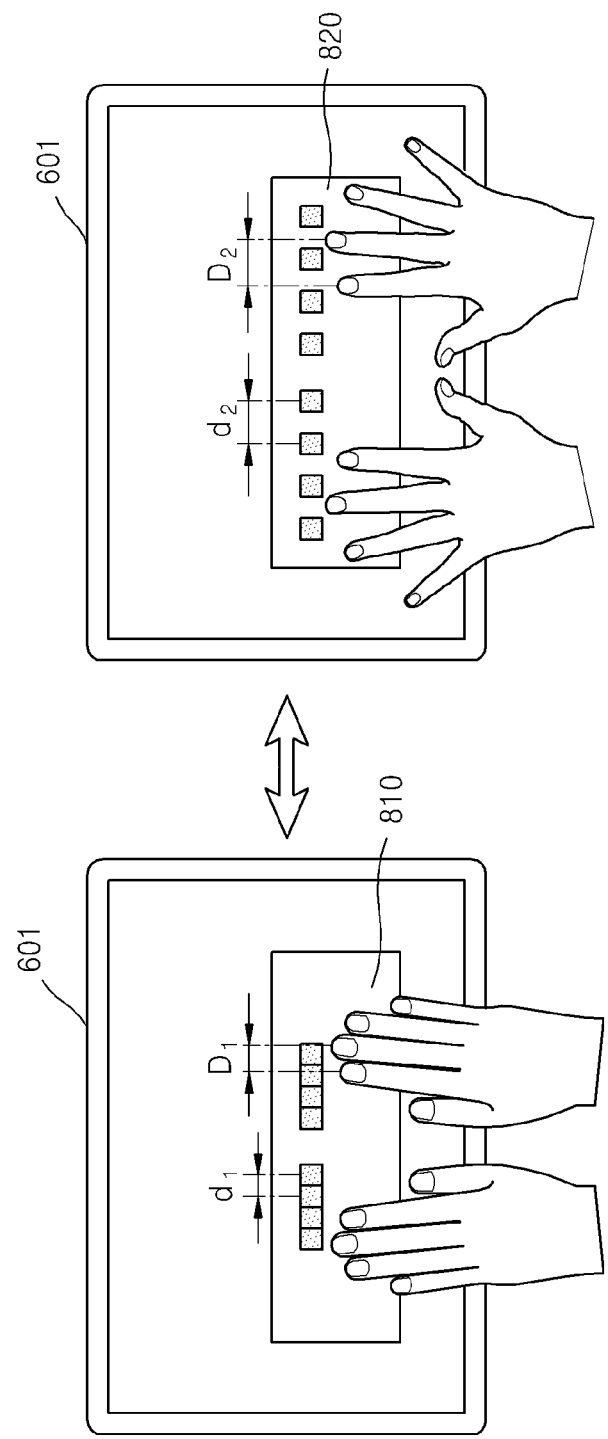
FIG. 8 illustrates an example of a virtual keyboard providing screen which enables a key interval to be adjusted and is provided through the UI providing apparatus according to an embodiment of the present invention.

FIG. 8 illustrates an example of a virtual keyboard providing screen which enables a key interval to be adjusted and is provided through the UI providing apparatus according to an embodiment of the present invention.

The UI providing apparatus 200 according to an embodiment of the present invention may decide to display a virtual keyboard on the screen 601 on the basis of the user's gesture.

At this time, the UI providing apparatus 200 may detect the user's hand gesture corresponding to the virtual keyboard, and moreover, may further detect an interval between fingertips. Furthermore, the UI providing apparatus 200 may adjust the virtual keyboard so as to have a key interval corresponding to the detected interval, and display the adjusted virtual keyboard on the screen 601.

As illustrated in FIG. 8, the UI providing apparatus 200 may detect an interval $D_1$ between at least two fingertips, and display a virtual keyboard 810 on the screen 601, the virtual keyboard 810 having a key interval $d_1$ corresponding to the detected interval $D_1$.

When an interval $D_2$ between fingertips is changed according to sizes of different hands of users or a user's intention, the UI providing apparatus 200 may display a virtual keyboard 820 on the screen 601, the virtual keyboard 820 having a key interval $d_2$ corresponding to the detected interval $D_2$.

The UI providing apparatus 200 may adjust a key interval of a virtual keyboard on the basis of an interval between specific two fingertips, or adjust the key interval of the virtual keyboard on the basis of an average interval between fingertips.

Therefore, a user using the UI providing apparatus 200 according to an embodiment of the present invention is provided with a touch input UI of which a key interval is automatically adjusted according to the user, and conveniently typewrites a keyboard, thus decreasing an error typewriting rate.

In FIG. 8, only an embodiment in which a key interval of a virtual keyboard is adjusted according to a size or posture of a user's hand is illustrated, but the present invention is not limited thereto. Even when a touch input UI instead of the virtual keyboard is provided, the UI providing apparatus 200 may provide a touch input UI where a posture or position of the user's hand has been adjusted based on the posture or position of the user's hand, thereby providing a personalized touch input UI suitable for the user.

The method according to the embodiments of the present invention can be implemented as computer readable codes in a computer readable medium. The computer readable recording medium may include a program instruction, a local data file, a local data structure, or a combination thereof. The computer readable recording medium may be specific to exemplary embodiments of the invention or commonly known to those of ordinary skill in computer software. The computer readable recording medium includes all types of recordable media in which computer readable data are stored. Examples of the computer readable recording medium include a magnetic medium, such as a hard disk, a floppy disk and a magnetic tape, an optical medium, such as a CD-ROM and a DVD, a magneto-optical medium, such as a optical disk, and a hardware memory, such as a ROM, a RAM and a flash memory, specifically configured to store and execute program instructions. Further, the computer readable recording medium may be implemented in the form of a transmission medium, such as light, wire or waveguide, to transmit signals which designate program instructions, local data structures and the like. Examples of the program instruction include machine code, which is generated by a compiler, and a high level language, which is executed by a computer using an interpreter and so on.

It should be understood that the exemplary embodiments described herein should be considered in a descriptive sense only and not for purposes of limitation. Descriptions of features or aspects within each embodiment should typically be considered as available for other similar features or aspects in other embodiments.

While one or more embodiments of the present invention have been described with reference to the figures, it will be understood by those of ordinary skill in the art that various changes in form and details may be made therein without departing from the spirit and scope of the present invention as defined by the following claims.

What is claimed is:

1. A user interface (UI) providing method for use in a medical diagnostic apparatus, the UI providing method comprising:
    detecting a number of hands and a number of fingers of a user;
    determining a touch input UI, from among a plurality of touch input UIs, that corresponds to the detected number of hands and number of fingers and is to be displayed on a screen; and
    adjusting and displaying the touch input UI on a basis of a distance from the screen to the hand,
    wherein the determining of the touch input UI comprises:
        when the number of the detected hands is two and the number of the detected fingers is eight or more, determining a virtual keyboard as the touch input UI;
        when the number of the detected hands is one and the number of the detected fingers is two, determining a time gain compensation (TGC) adjustment UI as the touch input UI;
        when the number of the detected hands is one and the number of the detected fingers is one, determining a menu selection UI as the touch input UI; and
        when the number of the detected hands is one and no finger is detected, determining an image control UI as the touch input UI.

2. The UI providing method of claim 1, wherein the adjusting and displaying of the touch input UI comprises changing at least one of transparency, size, and position of the touch input UI on a basis of the distance from the screen to the hand.

3. The UI providing method of claim 1, wherein the adjusting and displaying of the touch input UI comprises, as the distance from the screen to the hand becomes shorter, decreasing the transparency of the touch input UI.

4. The UI providing method of claim 1, wherein the adjusting and displaying of the touch input UI comprises:
    when the distance from the screen to the hand is equal to a first distance, displaying a portion of the touch input UI on the screen; and
    when the distance from the screen to the hand is equal to a second distance, displaying an entirety of the touch input UI on the screen, the second distance being shorter than the first distance.

5. The UI providing method of claim 1, wherein the adjusting and displaying of the touch input UI comprises changing at least one of a shape, color, brightness, and flickering period of the touch input UI on a basis of the distance from the screen to the hand.

6. The UI providing method of claim 1, further comprising:
    acquiring an image of the hand;
    detecting a change in at least one of a palm, knuckle, and fingertip of the hand from the acquired image; and
    searching for a gesture, corresponding to the detected change in the at least one of the palm, knuckle, and fingertip of the hand, from stored information about at least one gesture.

7. The UI providing method of claim 1, wherein the adjusting and displaying of the touch input UI comprises:
    detecting a position of the hand; and
    displaying the touch input UI on a region of the screen corresponding to the detected position.

8. The UI providing method of claim 1, wherein the touch input UI comprises at least one of a virtual keyboard, a time gain compensation (TGC) adjustment UI, a menu selection UI, and an image control UI that controls a rotation of a 3D medical image.

9. The UI providing method of claim 1, wherein when the touch input UI is a virtual keyboard, the adjusting and displaying of the touch input UI comprises:
    detecting an interval between fingertips of the hand; and
    displaying the virtual keyboard having a key interval corresponding to the detected interval.

10. A user interface (UI) providing apparatus for use in a medical diagnostic apparatus, the UI providing apparatus comprising:
    a detector configured to detect a number of hands and a number of fingers of a user;
    a controller configured to determine a touch input UI, from among a plurality of touch input UIs, which corresponds to the detected number of hands and number of fingers and is to be displayed on a screen, and adjusts the touch input UI on a basis of a distance from the screen to the hand; and
    a display configured to display the adjusted touch input UI,
    wherein,
        when the number of the detected hands is two and the number of the detected fingers is eight or more, the controller determines a virtual keyboard as the touch input UI,
        when the number of the detected hands is one and the number of the detected fingers is two, the controller determines a time gain compensation (TGC) adjustment UI as the touch input UI,
        when the number of detected hands is one and the number of the detected fingers is one, the controller determines a menu selection UI as the touch input UI, and
        when the number of the detected hands is one and no finger is detected, the controller determines an image control UI as the touch input UI.

11. The UI providing apparatus of claim 10, wherein the controller changes at least one of transparency, size, and position of the touch input UI on a basis of the distance from the screen to the hand.

12. The UI providing apparatus of claim 10, wherein as the distance from the screen to the hand becomes shorter, the controller decreases the transparency of the touch input UI.

13. The UI providing apparatus of claim 10, wherein, when the distance from the screen to the hand is equal to a first distance, the controller displays a portion of the touch input UI on the screen,
when the distance from the screen to the hand is equal to a second distance, the controller displays an entirety of the touch input UI on the screen, and
the second distance is shorter than the first distance.

14. The UI providing apparatus of claim 10, wherein the controller changes at least one of a shape, color, brightness, and flickering period of the touch input UI on a basis of the distance from the screen to the hand.

15. The UI providing apparatus of claim 10, wherein the detector comprises:
an image acquirer configured to acquire an image of the hand;
an image analyzer configured to detect a change in at least one of a palm, knuckle, and fingertip of the hand from the acquired image; and
a searcher configured to search for a gesture, corresponding to the detected change in the at least one of the palm, knuckle, and fingertip of the hand, from stored information about at least one gesture.

16. The UI providing apparatus of claim 10, wherein, the detector detects a position of the hand, and
the controller controls the UI display to display the touch input UI on a region of the screen corresponding to the detected position.

17. The UI providing apparatus of claim 10, wherein the touch input UI comprises at least one of a virtual keyboard, a time gain compensation (TGC) adjustment UI, a menu selection UI, and an image control UI that controls a rotation of a 3D medical image.

18. The UI providing apparatus of claim 10, wherein when the touch input UI is a virtual keyboard,
the detector detects an interval between fingertips of the hand, and
the controller controls the UI display to display the virtual keyboard having a key interval corresponding to the detected interval.

19. A non-transitory computer-readable storage medium storing a program for executing a user interface (UI) providing method for use in a medical diagnostic apparatus, the UI providing method comprising:
detecting a number of hands and a number of fingers of a user;
determining a touch input UI, from among a plurality of touch input UIs, that corresponds to the detected number of hands and number of fingers and is to be displayed on a screen; and
adjusting and displaying the touch input UI on a basis of a distance from the screen to the hand,
wherein the determining of the touch input UI comprises:
when the number of the detected hands is two and the number of the detected fingers is eight or more, determining a virtual keyboard as the touch input UI;
when the number of the detected hands is one and the number of the detected fingers is two, determining a time gain compensation (TGC) adjustment UI as the touch input UI;
when the number of the detected hands is one and the number of the detected fingers is one, determining a menu selection UI as the touch input UI; and
when the number of the detected hands is one and no finger is detected, determining an image control UI as the touch input UI.

* * * * *